US006483583B1

(12) United States Patent
Wright et al.

(10) Patent No.: US 6,483,583 B1
(45) Date of Patent: Nov. 19, 2002

(54) NEAR INFRARED SPECTROMETRY FOR REAL TIME ANALYSIS OF SUBSTANCES

(75) Inventors: Steven L. Wright, West Des Moines, IA (US); Thomas B. Brumback, Jr., Alleman, IA (US); William S. Niebur, Des Moines, IA (US); Roland Welle, Buxtehude (DE)

(73) Assignee: Textron Systems Corporation, Wilmington, MA (US)

( * ) Notice: Subject to any disclaimer, the term of this patent is extended or adjusted under 35 U.S.C. 154(b) by 0 days.

(21) Appl. No.: 09/309,157

(22) Filed: May 10, 1999

Related U.S. Application Data

(63) Continuation-in-part of application No. 09/075,614, filed on May 11, 1998, now Pat. No. 5,991,025, which is a continuation-in-part of application No. 08/807,661, filed on Feb. 27, 1997, now Pat. No. 5,751,421.

(51) Int. Cl.[7] .............................. G01J 3/28; A01F 12/00
(52) U.S. Cl. ............................. 356/326; 356/328; 460/7
(58) Field of Search ................. 356/402–411, 330–334, 356/326, 328; 250/226, 339.12, 339.11; 460/4, 6, 7

(56) References Cited

U.S. PATENT DOCUMENTS

| | | | |
|---|---|---|---|
| 3,597,616 A | 8/1971 | Brunton et al. | 250/331.06 |
| 4,040,747 A | 8/1977 | Webster | 356/418 |
| 4,253,766 A | 3/1981 | Funk | 356/418 |

(List continued on next page.)

FOREIGN PATENT DOCUMENTS

| | | | |
|---|---|---|---|
| SU | 1467470 A1 | 3/1989 | |
| WO | WO 85/00087 | 1/1985 | |
| WO | wo 92/15192 | 9/1992 | |

OTHER PUBLICATIONS

Carol R. Dumas; Analyzer Packs Protein Punch; Intermountain Farm & Ranch; Feb. 7, 1997; 3 pgs.
Francis J. Pierce, Michigan State Univ.; Quality Maps; ag/Innovator; 10/95; 1 pg.
P. Dardenne et al., *Evaluation of NIT for Predicting Fresh Forage Quality*, Proceedings of the Vth Int'l. Conference of NIRS in Aberdeen, Scottland; ©1991; pp. 277–283.
P. Dardenne, R. Agneessens & G. Sinnaeve., *Fresh Forage Analysis by Near Infrared Spectroscopy*, Proceedings of the Viith Int'l. Conference of NIRS in Montreal, Canada; ©1995; pp. 531–536.
Rosenthal, "Characteristics of Non–Destructive Near–Infrared Instruments for Grain and Food Products", 1986 Meeting Japan Food Service Institute, pp. 1–23.
G. Sinnaeve et al., *The Use of Near Infrared Spectroscopy for the Analysis of Fresh Grass Silage*, 1994, pp. 79–84, NIR Publications.
Derwent 89–276737/38 for SU1467–470 Abstract; Bul. 11/23.3.89; Dtd. Unknown—(See IDS 7–A).

*Primary Examiner*—Michael P. Stafira
(74) *Attorney, Agent, or Firm*—Lesley A. Hamlin

(57) ABSTRACT

An apparatus and method for utilizing NIR spectrography for measuring major constituents of substances in real time includes a monochromator or other sensor having no moving optical parts. At least one of the monochromator and the substance are moving relative to one another. An NIR radiation source irradiates a substance and the reflected or passed-through radiation is transmitted to the monochromator, which isolates and detects narrow portions of the received spectrum. By analyzing the intensities and wavelengths of the received radiation, the presence and amount of major constituents of the substance can be determined.

26 Claims, 16 Drawing Sheets

U.S. PATENT DOCUMENTS

| | | | |
|---|---|---|---|
| 4,260,262 A | | 4/1981 | Webster ................... 356/418 |
| 4,400,086 A | | 8/1983 | Webster ................... 356/36 |
| 4,441,513 A | | 4/1984 | Herwig ................... 460/1 |
| 4,463,261 A | | 7/1984 | Bowman ................... 250/339.1 |
| 4,560,275 A | | 12/1985 | Goetz ................... 356/326 |
| 4,752,689 A | | 6/1988 | Satake ................... 250/339.07 |
| 4,806,764 A | | 2/1989 | Satake ................... 250/339.07 |
| 4,883,963 A | * | 11/1989 | Kemeny et al. ................... 250/339 |
| 4,925,305 A | | 5/1990 | Erickson ................... 356/300 |
| 4,997,280 A | | 3/1991 | Norris ................... 356/308 |
| 5,038,040 A | * | 8/1991 | Funk et al. ................... 250/341 |
| 5,040,889 A | | 8/1991 | Keane ................... 250/339.09 |
| 5,050,989 A | * | 9/1991 | Van Tassel et al. ................... 356/310 |
| 5,132,538 A | | 7/1992 | Norris ................... 250/339.11 |
| 5,239,180 A | | 8/1993 | Clarke ................... 250/339.02 |
| 5,241,178 A | | 8/1993 | Shields ................... 250/339.11 |
| 5,308,981 A | | 5/1994 | Perten ................... 250/339.02 |
| 5,327,708 A | | 7/1994 | Gerrish ................... 250/339.11 |
| 5,406,084 A | | 4/1995 | Tobler et al. ................... 56/1 |
| 5,448,069 A | | 9/1995 | Tobler et al. ................... 250/339.61 |
| 5,475,221 A | * | 12/1995 | Wang ................... 250/339.07 |
| 5,480,354 A | | 1/1996 | Sadjadi ................... 460/7 |
| 5,517,302 A | | 5/1996 | Stearns et al. ................... 356/326 |
| 5,751,421 A | | 5/1998 | Wright et al. ................... 356/328 |
| 5,991,025 A | | 11/1999 | Wright et al. ................... 356/328 |
| 6,100,526 A | | 8/2000 | Mayes ................... 250/339.11 |

* cited by examiner

NEAR INFRARED SPECTROMETRY FOR REAL TIME ANALYSIS OF SUBSTANCES

CROSS-REFERENCE TO RELATED APPLICATION

This is a continuation-in-part of application Ser. No. 09/075,614 filed May 11, 1998, now U.S. Pat. No. 5,991,025, which was a continuation-in-part of application Ser. No. 08/807,661 filed on Feb. 27, 1997, now U.S. Pat. No. 5,751,421.

BACKGROUND OF THE INVENTION

1. Field of the Invention

The present invention relates to methods and apparatus for measuring constituents of substances and products. More particularly, though not exclusively, the present invention relates to a method and apparatus using near infrared spectrometry for real time product analysis.

2. Problems in the Art

In the field of agriculture, it is important to analyze agricultural products such as grain or forage to determine the amount of major constituents in the products. This is particularly important in breeding programs.

One prior art method of analyzing grain and other agricultural products is using near infrared spectroscopy (NIR). NIR is a well-established technique for detecting both chemical and physical properties of various materials. NIR provides an accurate and inexpensive method to analyze agricultural materials such as grain or forage. Major constituents that can be detected by using NIR include moisture, protein, oil, starch, amino acids, extractable starch, density, test weight, digestibility, cell wall content, and any other constituents or properties that are of commercial value.

There are various types of devices used for NIR. In general, these devices include light sensors in conjunction with light sources, which are used with any number of measuring devices. In optical spectrometers, the incident light from a light source is passed through a monochromator, which can be a filter or set of filters, a diffraction grating, or a prism whose angular displacement relative to the incoming light can be closely correlated with the single wavelength, or narrow band of wavelengths (which it sends on to the light sensor). The light sensor is selected so that its spectral responses match the wavelength of interest. The angular motion of the prism or diffraction grating can be mechanized so that a given spectrum is scanned at a known rate over a known time interval. Such a device is referred to as a scanning spectrometer. The wavelength of an observed peak can then be determined from the time counted from the start of a scan. Spectrometers may also be referred to as spectrophotometers when their spectral range extends between ultraviolet to infrared.

The constituent content of a grain sample, for example, is measured most accurately by prior art systems by drying and grinding the sample of the grain to particulate form. The ground sample is then irradiated with near infrared light. The reflected radiation is detected at narrow band wavelengths in the NIR spectrum to obtain raw reflectance data of the sample. The data can be used to provide accurate measurements of the content of constituents of the grain samples. In many prior art systems, it is difficult to obtain accurate measurements of the grain constituents without first drying and grinding the grain into particulate form.

Other prior art systems use scanning or oscillating spectrophotometric instruments. In such an instrument, a photo detector detects light energy, which is scanned through a spectrum at a rapid rate. Such an instrument employs an optical grating, which receives light through an entrance slit and disperses the light into a spectrum directed toward an exit slit. The optical grating is oscillated in order to rapidly scan the light transmitted through the exist slit through the spectrum dispersed by the grating. Another prior art instrument uses filters, which are tilted as they pass through a light beam to scan the transmitted light through a spectrum. Either type of instrument, the oscillating optical grating or the tilt filter type can be operated over a spectrum covering near infrared to analyze agricultural products such as grain. Using an oscillating grating or tilting filter type of instrument, the user can measure the reflectivity of the sample at narrow wavelength increments to determine the constituent contents of a grain sample. To use an oscillating grating or tilting filter instrument, the narrow bandwidth light is transmitted through the exit slit used to illuminate the grain sample. The light reflected from the sample is detected by photo detectors and the resulting photo detector signal is used to determine the constituent contents of the sample. As the grating oscillates, the center frequency of the light that irradiates the sample is swept through the NIR spectrum. Light from the diffraction grating that is reflected by the sample is detected by the photo detector. As an alternative to detecting the energy reflected from the sample, the energy may be transmitted through the sample and detected after being transmitted through the sample. In addition, instead of irradiating the sample with the output from the spectrophotometer, the sample can be irradiated with constant wide-band light and a reflected light being applied to the spectrophotometer.

If a grain sample is not ground, the light absorbency and reflectance varies considerably from sample to sample. This variation is caused by light scatter from the whole grain kernels and by the nonlinear surface reflectance effects. This variation makes it difficult to obtain accurate measurements from whole grain samples. Similar problems are encountered with forage samples, especially corn forage, but even more pronounced.

The spectrometers discussed require frequent calibration in order to generate accurate results. The calibrations must be performed frequently due to various dynamic factors including the change in light from a light source due to temperature sources. A typical method of calibrating (to correct for instrument response variation by baseline correction) a spectrometer is to replace the sample with a standard sample, for example, a white ceramic tile having high reflectance. The spectrometer scans the standard sample to provide standard values, which are used to calibrate the spectrometer. While this calibration method works fine in a lab environment, it could be impossible, or at least impractical in the environment of an agricultural implement such as a combine or a chopper.

The spectrometers discussed above have several disadvantages. The spectrometers discussed are only suitable for use in a laboratory. Prior art methods of grain analysis have a major disadvantage resulting from the large amount of sample handling. The samples must be harvested, collected, bagged, labeled, dried, and finally sent to the NIR lab, ground and analyzed for constituent analysis. This excessive sample handling adds both cost and time to the analysis. A need can therefore be seen for an NIR instrument combined with an implement such as a combine or chopper to automate the process of collecting an analyzing grain and forage samples. Such a system would reduce the cost and time of the analysis. Such a system could provide plant breeders and grain farmers with real time information and also enhance product development through high plot screening numbers, which would help develop products more rapidly.

The main problem with an NIR instrument combined with a machine such as a combine or chopper is that prior art grain or forage analysis instrumentation is very sensitive to mechanical vibrations. Scanning and oscillating spectrometers require very precise mechanical movements in order to obtain accurate results. The extreme vibrations found in the environment of a combine or chopper would result in damaged and inaccurate instrumentation equipment. In addition to the vibration, the combine or chopper environment is very dirty. The amount of dust and plant debris would severely effect the effectiveness of a conventional spectrometer.

Another problem with combining NIR instrumentation with an implement is that current NIR equipment requires a long time period for analysis. In the field of crop breeding programs, a large number of test plots are used to test products. A typical test plot of hybrid corn, for example, is comprised of two rows of corn with a length of 17 ft. A research combine used to harvest the test plots goes through each test plot in approximately 15 seconds. A typical spectrometer used in a lab to analyze grain requires more time than 30–90 seconds to analyze the grain or forage sample. Therefore, even if conventional NIR instrumentation is installed on an implement, the speed of harvesting test plots would be slowed down considerably by the slow speed of the NIR instrumentation.

A need can therefore be seen for NIR equipment in combination with an implement such as a combine or chopper which could operate effectively in the environment of a combine or chopper which also is capable of analyzing product samples in a short period of time.

Similar problems exist for other applications and functions where it would be beneficial to be able to analyze constituents of substances in non-laboratory settings. For example, it would be beneficial to be able to non-destructively, in essentially real time, determine constituents of substances when either the measurement equipment or the substance are moving relative to one another, or even when both are moving. An example is pre-harvested agricultural products. The sugar content of grapes growing on the grape vine could be measured by moving equipment by the vines on a vehicle. Another example is nutraceuticals. Nutraceuticals are plants that internally induce the production of pharmaceutically active components. It would valuable to be able to quickly and non-destructively evaluate such production by moving measurement equipment past the growing plants.

Another example relates to harvested agricultural products. Non-destructive, real time measurement of constituents during harvesting, during movement through a harvester machine, during handling such as unloading to a transport vehicle, during storage, during transport to another location, or even during further processing would advantageous.

Whether measurement occurs pre-harvest or post-harvest, benefits could be obtained for such things as hybrid development or breeding programs. Results could be stored and analyzed and compared.

In most of the above examples, the measurements would be taken in environments that would include physical forces such as vibration or potentially damaging or disruptive materials such as dust and debris. Such non-laboratory conditions are particularly problematic because environmental conditions can change quickly and repeatedly.

Other examples exist. Soil analysis in real time without taking soil samples would be beneficial. Therefore, there is room for improvement in the art.

FEATURES OF THE INVENTION

A general feature of the present invention is the provision of a method and apparatus for measuring constituents of products in real time, which overcomes problems, found in the prior art.

A further feature of the present invention is the provision of a method and apparatus for measuring constituents of products which uses a monochromator which is robust, an example being a stationary grating with a photodiode array with a detector which has no moving optical parts and thus is more resilient to mechanical vibrations.

A further feature of the present invention is the provision of a method and apparatus for measuring constituents of products, which is capable of measuring the constituents in a short time period or is essentially real time.

Further features and advantages of the present invention include:

An apparatus and method of measuring the constituents of products which analyzes the products while the products are flowing or moving or while the measuring apparatus or steps are moving relative to the products, or both are moving.

An apparatus and method of measuring the constituents of products in which the monochromator is optically communicated to the product by a fiber optic connection.

An apparatus and method of measuring the constituents of products using the reflectance of radiation from the agricultural product or radiation after passing through the product.

An apparatus and method of measuring the constituents of products which measures the constituents in real time and stores the measurements for later use.

An apparatus and method of measuring the constituents of products which can be automatically calibrated.

An apparatus and method of measuring the constituents of products which senses the reflectance of the sample in more than one position in order to obtain higher accuracy.

An apparatus and method of measuring the constituents of products which can be used in non-laboratory settings including where environmental conditions can result in the measuring experiencing physical forces or dust and debris.

An apparatus and method of measuring the constituents of products which can be used in non-laboratory settings including where environmental conditions can change over time.

An apparatus and method of measuring the constituents of products which is highly flexible and applicable to a variety of substances and uses.

An apparatus and method of measuring the constituents of products which is durable.

An apparatus and method of measuring the constituents of products which is non-destructive of the substance to be measured. These as well as other features and advantages of the present invention will become apparent from the following specification and claims.

SUMMARY OF THE INVENTION

The present invention relates to a method and apparatus for measuring constituents of substances or products. The invention uses near infrared spectroscopy. A radiation source is used to irradiate a product while reflected or passed-through radiation is collected and measured with a sensor located within, near, or adjacent to the substance. A spectral separator or a monochromator, for example a diffraction grating or its equivalent which spreads the infrared light over a desired wavelength band, isolates narrow portions of the spectrum of received radiation. A detector analyzes the intensities of the radiation at various isolated portions of the spectrum. From this information, the major constituents of the substance or product can be determined. The measurement apparatus or steps can be in motion relative to the substance being measured or vice versa, or both can be moving.

DETAILED DESCRIPTION OF THE PREFERRED EMBODIMENT

The present invention will be described as it applies to its preferred embodiment. It is not intended that the present invention be limited to the described embodiment. It is intended that the invention covers all alternatives, modifications, and equivalencies, which may be included within the spirit and scope of the invention.

Figure 1:
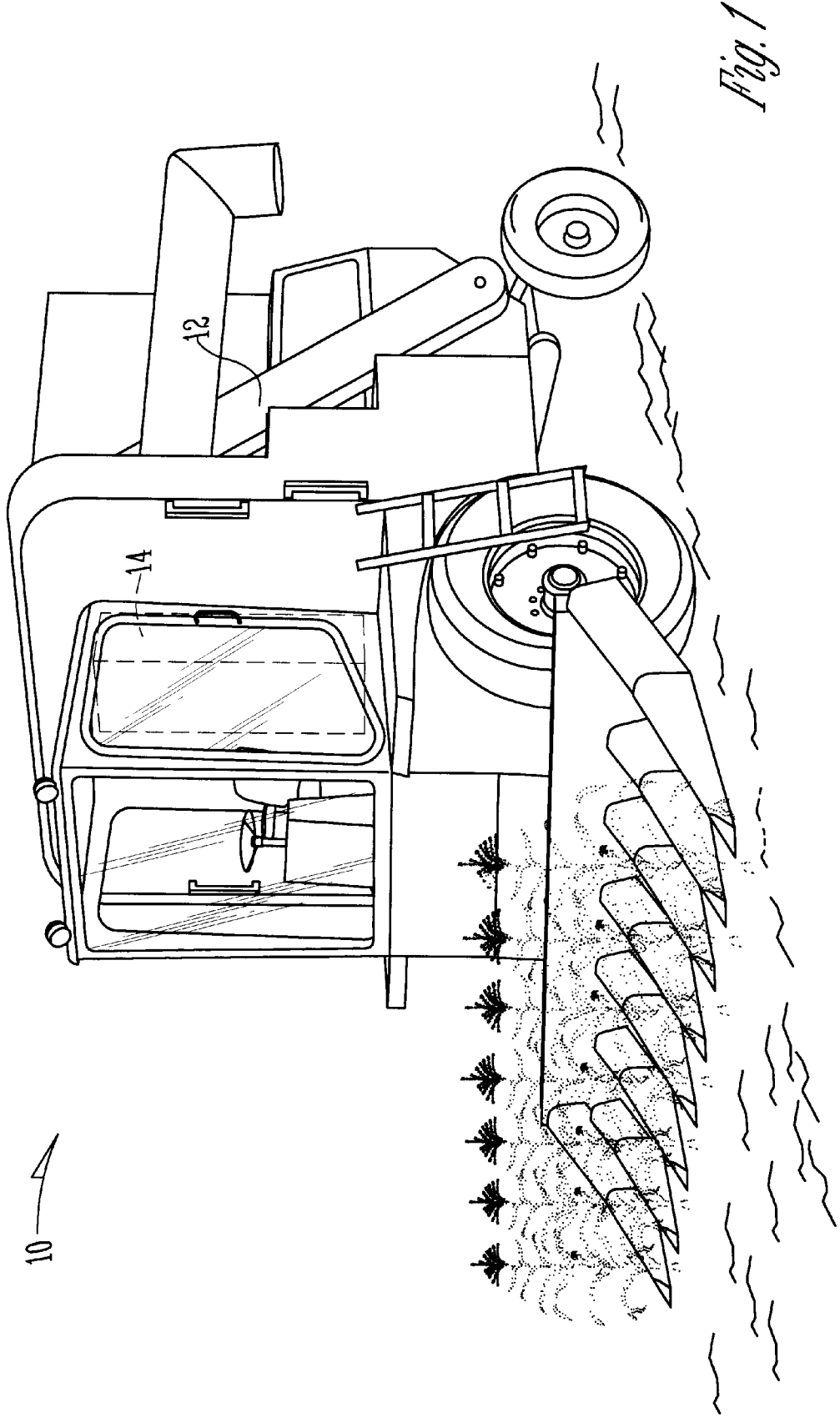
FIG. 1 is a perspective view of a research combine utilizing the present invention.

FIG. 1 shows a typical research combine 10, which may be used with the present invention. A research combine 10 is used by the plant hybrid industry or seed industry to harvest test plots and to evaluate the harvested grain. The combine 10 is similar to a standard combine but is adapted to take samples of the grain from the test plots and analyze properties of the grain in the field. The combine 10 includes a sample elevator 12 which moves grain to a test chamber assembly 14 which is shown in detail in FIGS. 2 and 3.

Figure 2:
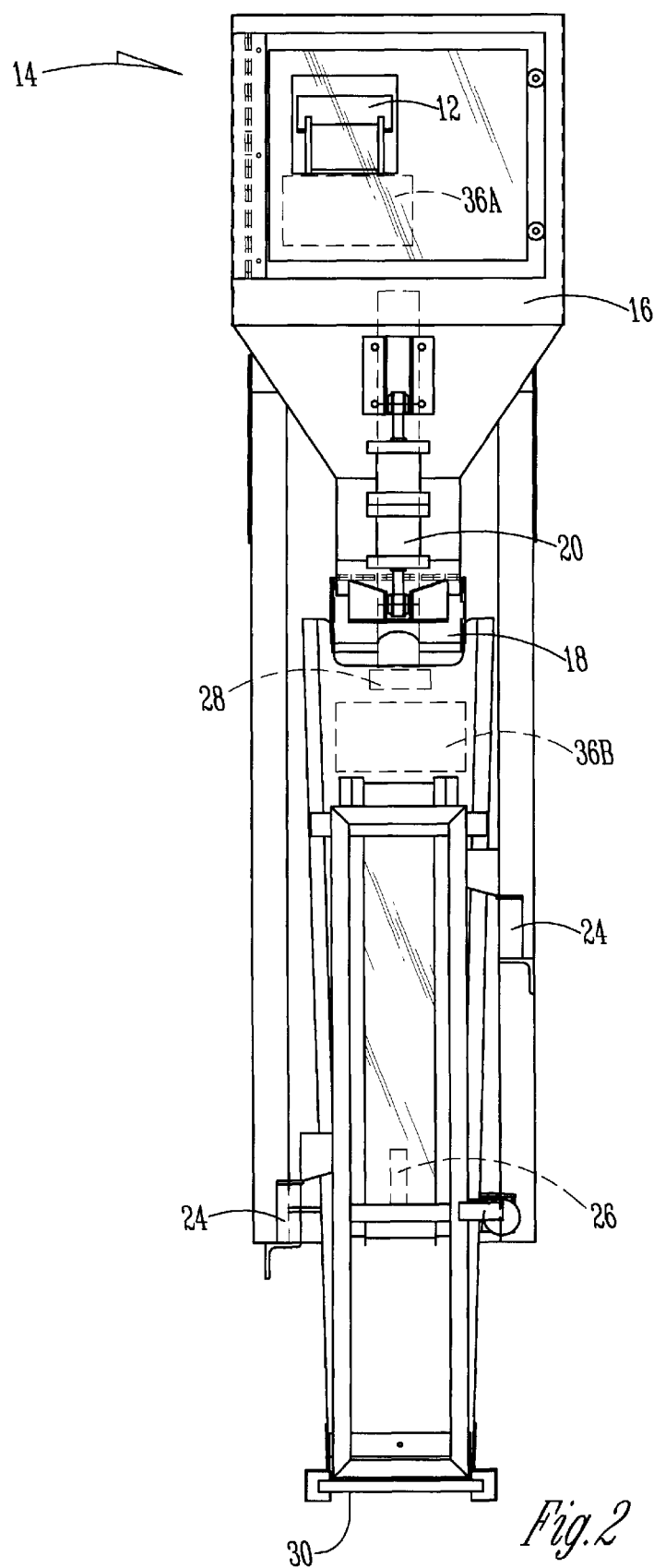
FIG. 2 is a front view of the test chamber assembly of the combine shown in FIG. 1.
Figure 3:
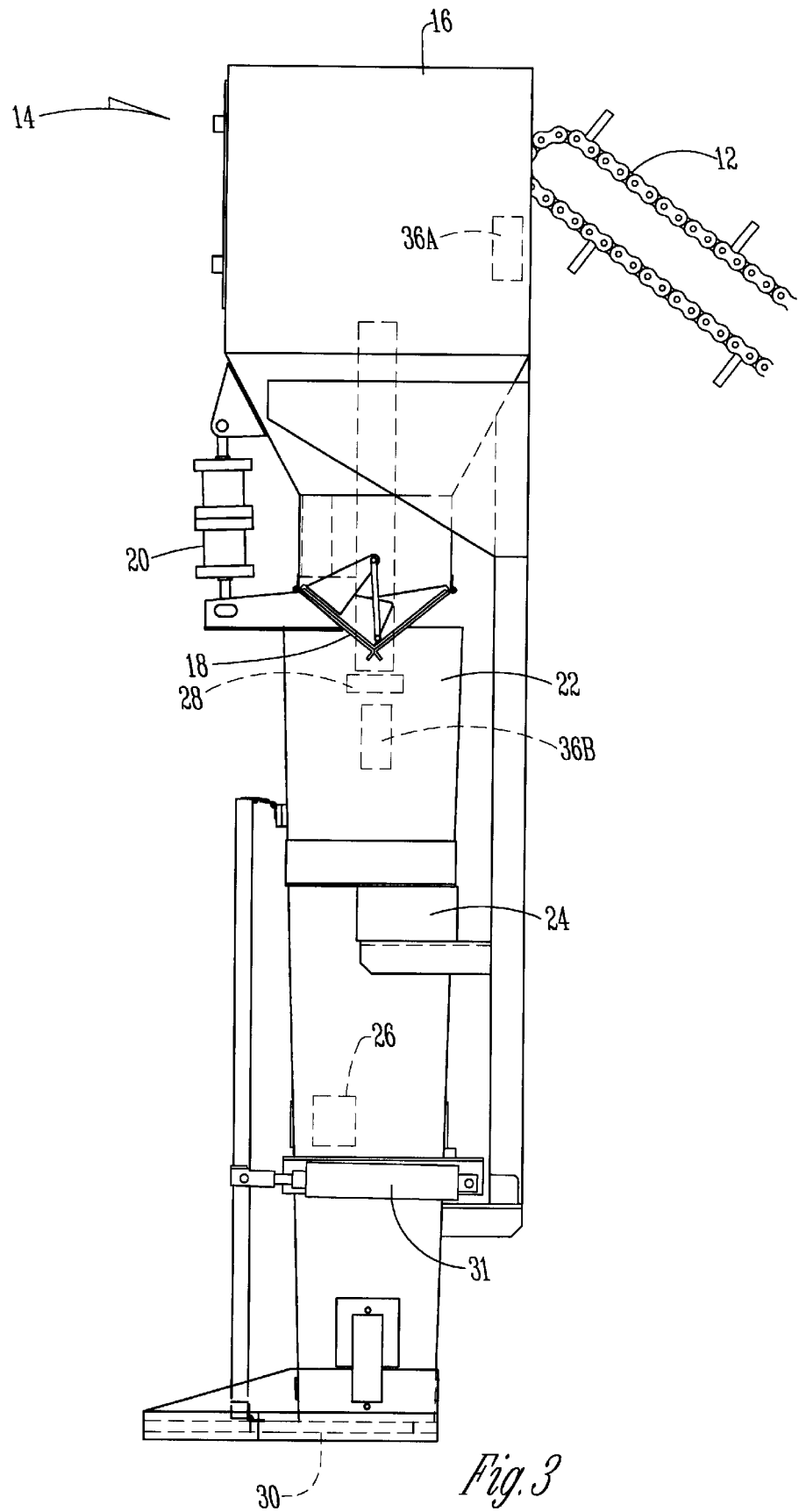
FIG. 3 is a side view of the test chamber assembly of the combine shown in FIG. 1.

The test chamber assembly 14 is designed to collect a sample of grain and to evaluate the grain to determine various properties of the grain. As shown in FIGS. 2 and 3, the grain enters the test chamber assembly 14 from the top from the elevator 12. After the grain falls off the elevator 12, it is collected in a chute 16. A door 18 prevents the grain from leaving the chute 16. The door 18 is controlled by a pneumatic door cylinder 20. The door 18 is controlled by the door cylinder 20 and moves from an opened to a closed position or any position in-between. When the door 18 is opened, the grain will fall into the test chamber 22. When the grain is in the test chamber 22, the sample is analyzed in a number of conventional ways. One or more load cells 24 are used to determine the weight of the grain within the chamber 22. A moisture sensor 26 is used to sense the moisture of the grain. A sonar device 28 is positioned above the chamber 22 and can determine how full the chamber is in order to determine the volume of grain in the chamber 22. Once these measurements are taken, an exit door 30 can be opened to empty the test chamber 22 so that a sample from the next test plot can be taken. The door 30 is controlled by an actuator 31 and its related linkages. A typical test plot of corn, for example, has two rows of corn each seventeen feet long. It takes the research combine 10 approximately fifteen seconds to harvest each test plot, so all the grain analysis must be completed within fifteen seconds.

Figure 4:
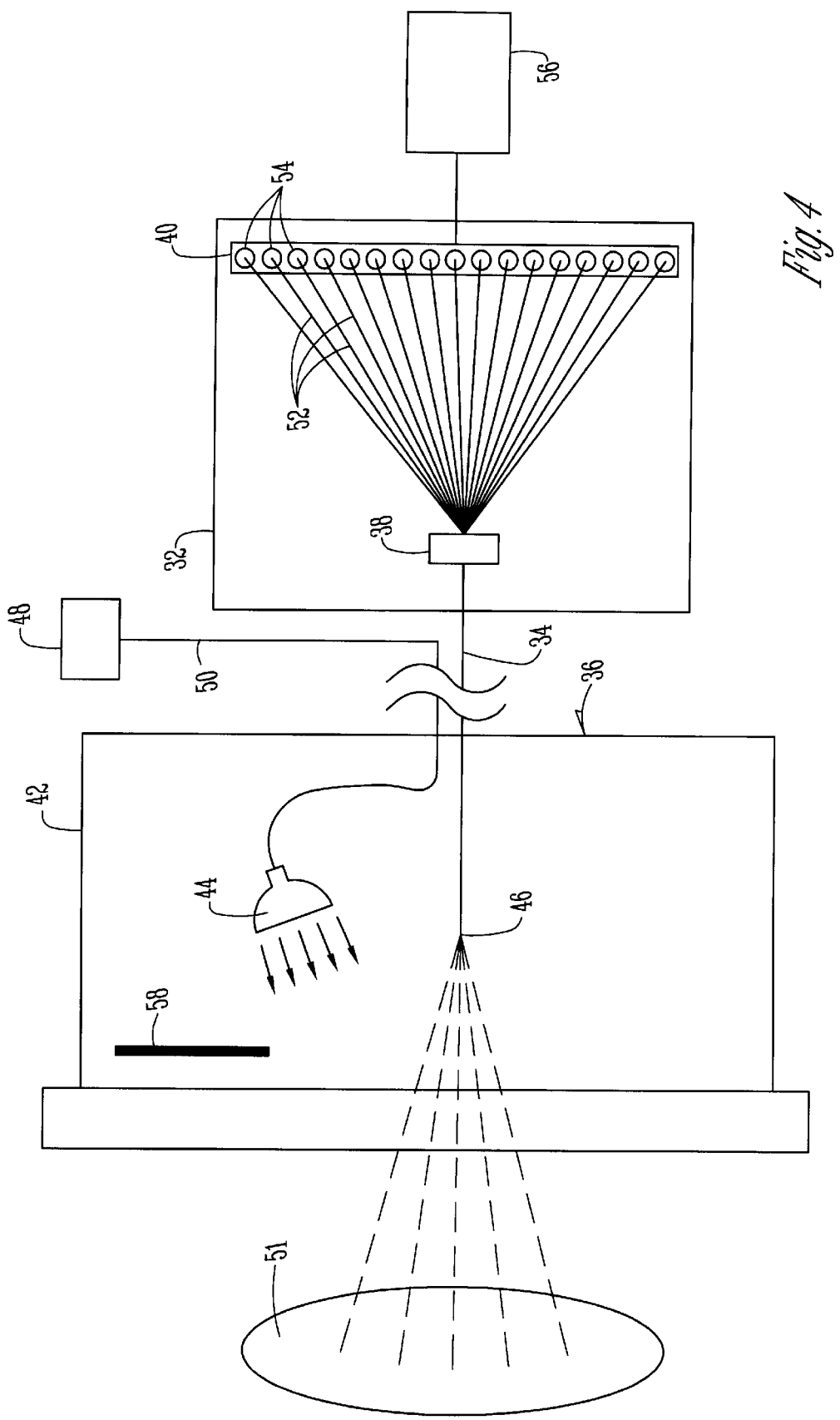
FIG. 4 is a block diagram of the present invention.

FIG. 4 is a block diagram of the present invention. FIG. 4 shows how the test chamber assembly 14 is used with the present invention. A monochromator 32, located in or near the cab of the combine 10, is connected to a fiber optic cable 34. The other end of the fiber optic cable 34 is connected to a sensor head 36. The sensor head 36 can be located in a number of locations relative to the test chamber assembly 14. FIGS. 2 and 3 show two possible locations for the sensor head 36. In a first location, a sensor head 36A is located below the elevator 12 and senses the grain as it falls into chute 16. In a second location, a sensor head 36B can be accurately controlled by controlling the amount the door 18 is opened. Preferably, the area around the sensor head 36 is enclosed to limit the amount of stray light, which affects the performance of the sensor head 36.

The monochromator 32 used with the present invention includes a fixed diffraction grating 38 and a photodiode array 40. It is important to note that because the photodiode array 40 is used, the monochromator 32 includes no moving optical parts. This is desired in order to withstand the extreme vibrations present in the environment of a combine. The photodiode array 40 also greatly increases the speed at which a sample can be analyzed since the entire desired spectrum of reflected light is transmitted at once, rather than scanning and transmitting one range at a time. The monochromator 32 is connected to a sensor head 36 by a bundle of fiber optic cables 34. While the fiber optic cable 34 could take on many forms, preferably the cable is comprised of 25 individual fiber optic strands.

Figure 5:
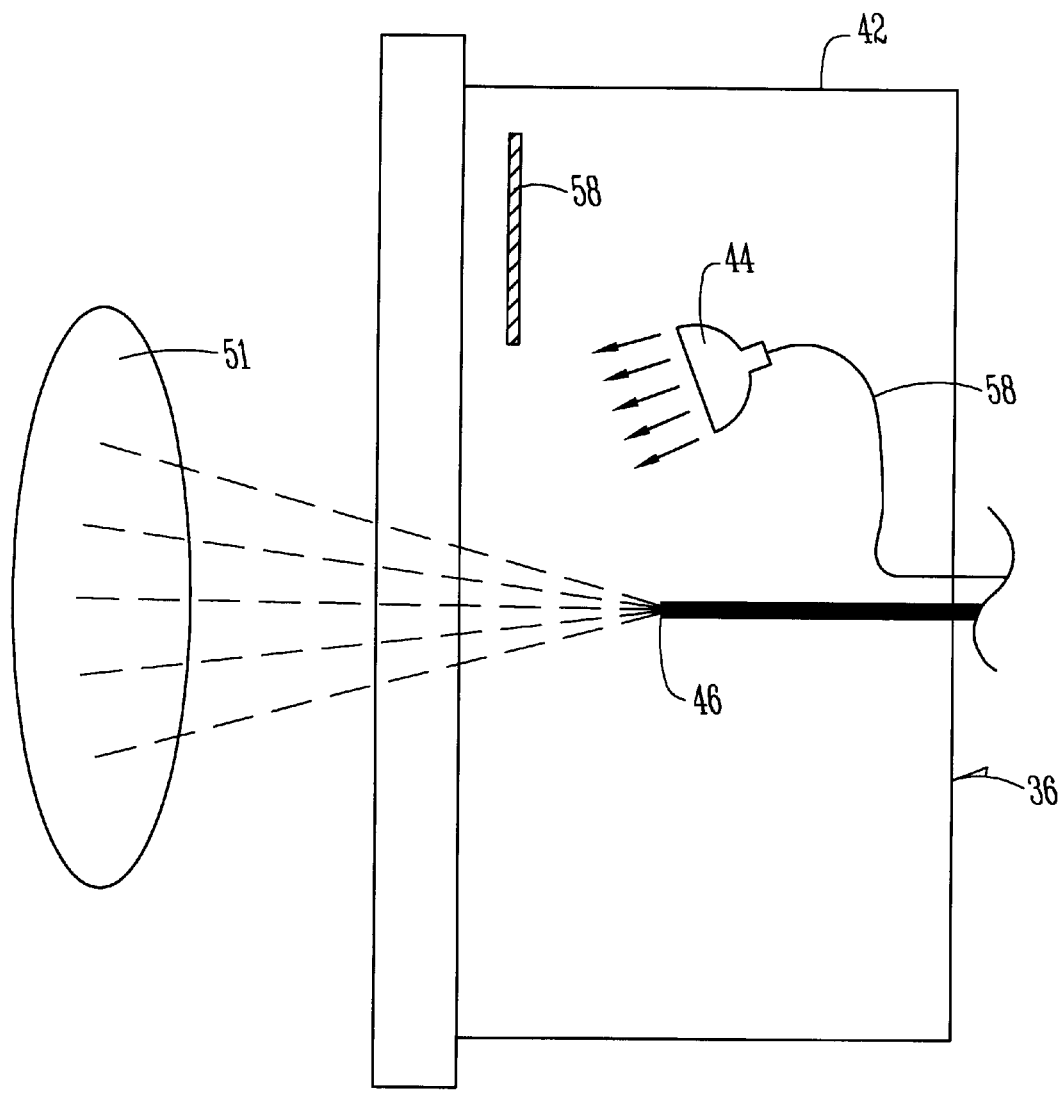
FIG. 5 is an enlarged view of the sensor head shown in FIG. 4.

FIG. 5 is an enlarged view of the sensor head 36. The sensor head 36 is comprised of a housing 42, which encloses a lamp 44 and a sensor 46. The sensor 46 could take on many forms, but preferably is simply comprised of the ends of the fiber optic strands of the fiber optic cable 34. The lamp is powered by a power source 48 (FIG. 4) which could be provided by the combine 10 or the monochromator 32. The power source is connected to the lamp 44 by a power cable 50 which is preferably bundled with the fiber optic cable 34 to reduce the number of cables between the sensor head 36 and the monochromator 32. The lamp 44 is preferably a halogen lamp, which provides a wide spectrum of radiation including radiation in the desired bandwidth, 400 to 1700 nanometers (nm). The lamp 44 is aimed at a desired angle towards the grain samples (discussed below). FIG. 5 also shows a white reference tile 58. The white reference tile 58 has a known reflectance and therefore can be used to calibrate the present invention. For the purposes of this description, the term "calibration" does not mean finding a correlation between optical densities and constituent percentage, but rather means to correct for instrument response variations be baseline correction.

The light sensor 46 is also positioned at a desired location relative to the grain sample 51 and lamp 44 (discussed below). When the lamp 44 irradiates the grain sample with light, some of the radiation is reflected off the grain sample toward the sensor 46. The reflected light is transmitted through the fiber optic cable 34 to the diffraction grating 38 in the monochromator 32 (FIG. 4). The diffraction grating scatters the light over an infinite number of paths represented by lines 52. The photodiode array 40 includes 512 photo detectors 54, which are disposed along the photodiode array 40. For purposes of clarity in the drawings, all 512 photo detectors 54 are not shown. Each photo detector 54 will receive light from the diffraction grating over just a small range of wavelengths. The diffraction grating and photo detectors 54 are arranged in the monochromator 32 so that light with a spectral range of 400 through 1700 nanometers is distributed along the array 40. It can be seen that by using a photodiode array with 512 photo detectors 54, the "scanning" time goes down by a factor of 512 compared to the prior art scanning spectrometer. The photodiode array 40 is connected to a processor 56, which collects data from the photodiode array 40 and stores and analyzes the data.

The present invention improves on accuracy and speed over the prior art. To help improve accuracy of the system, the grain sample presentation is made constant and repeatable. This results in consistent results. The samples are sensed in the same way and in the same location for each successive sample. In a lab, lab technicians may not analyze different samples in exactly the same way. A more consistent result is obtained by automating the analysis process. Also, sensing the samples as the grain is moving improves the accuracy and reliability since an "average" sample is taken, rather than looking at still kernels which have surfaces that vary from one part of the kernel to the other. Since the samples can be analyzed at a high rate of speed, the processor can average a number of readings to obtain a consistent result for each sample. For example, if the monochromator outputs spectrum data every 34 msec, then the processor can average 100 successive spectrums together and output a more reliable and stable spectrum every 3.4 seconds.

The present invention operates as follows. When harvesting a test plot, the research combine 10 harvests the grain in the test plot in a conventional manner. Referring to FIGS. 2 and 3, as grain from the harvested test plot enters the test chamber assembly 14 from the sample elevator 12, the chute 16 is filed with a sample of the grain. When the chamber 22 is ready for loading, the chute door 18 is opened by activating the door cylinder 20. The sensor head 36B of the present invention is located slightly below the door 18 and senses the grain as it flows past the sensor head 36B. The door 18 is opened a predetermined amount to allow an even flow of grain past the sensor head 36B. As the grain flows past the sensor head 36, light from lamp 44 is irradiated on the grain sample with some of the light reflecting off the grain sample to the sensor 46 (FIG. 5). The reflected light is transmitted through the fiber optic bundle 34 to a diffraction grating 38 in the monochromator 32, which is located within or near the cab of the combine 10 (FIG. 4). The diffraction grating 38 spreads the reflected light over the photodiode array 40 in a spectrum ranging from approximately 400 nanometers to 1100 nm in wavelength. A processor 56 is connected to the photodiode array and collects data relating to the strength of radiation at each individual photodiode 54. By analyzing the strength of the radiation at each photodiode 54, the processor can determine the amount of constituents in the sample of grain. For example, if the radiation strength at a certain photodiode is relatively low, then it can be determined that the grain sample has absorbed an amount of radiation at that wavelength. By knowing what certain substances absorb or reflect, it can be determined what substances are present in the sample. The data collected from the monochromator 32 is processed by the processor 56 and/or stored for later use. Once all the grain from the chute 16 has fallen into the test chamber 22, the test assembly 14 will evaluate the grain for weight, moisture, volume, etc., using conventional methods as discussed above. In this way, the sample of grain from a given test plot can be thoroughly evaluated including the grain sample weight, moisture, volume, and amount of major constituents present.

Figure 10:
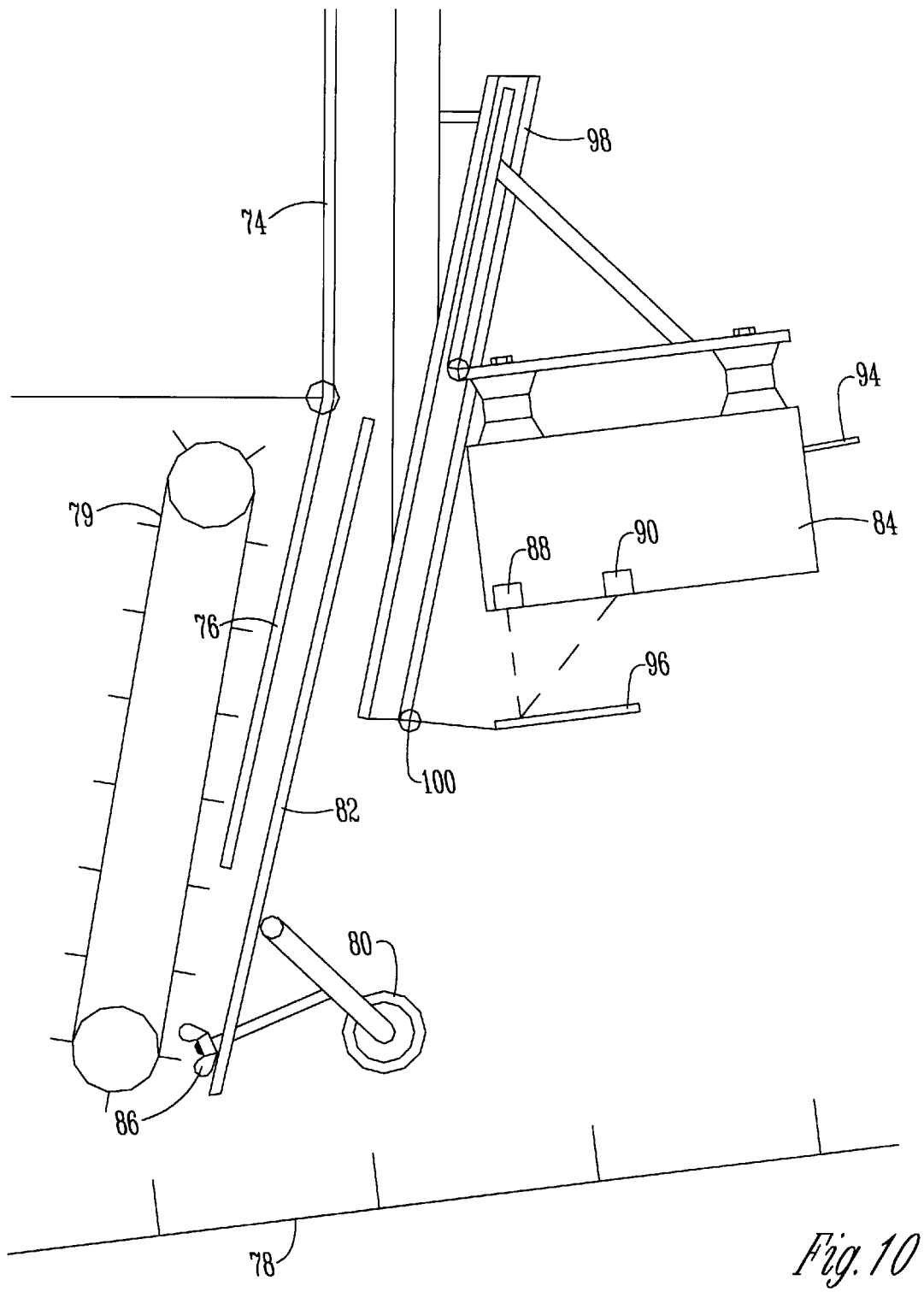
FIGS. 10–11 are views showing the calibration of the invention shown in FIG. 9.
Figure 11:
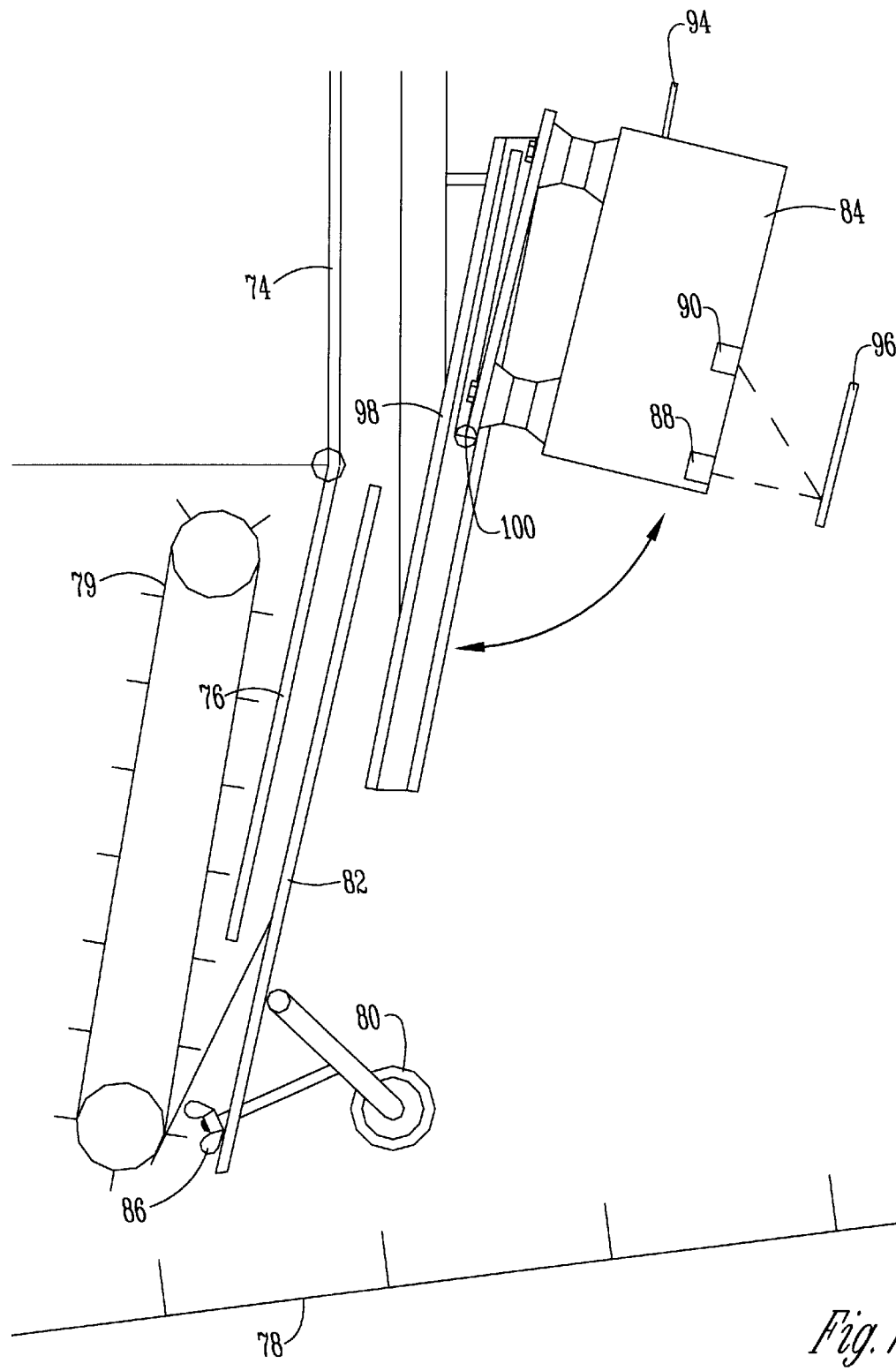
Figure 12:
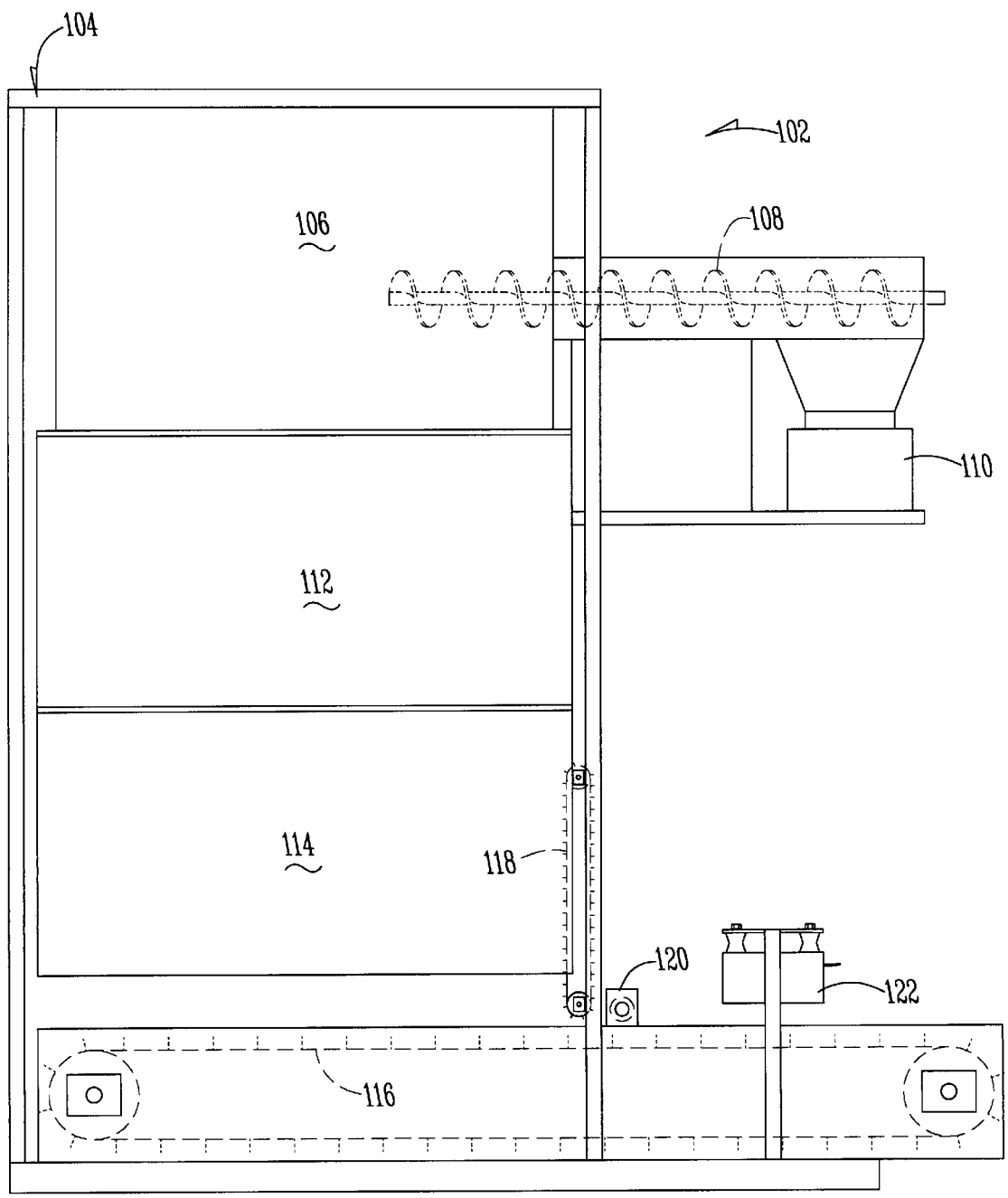
FIGS. 12 and 13 show a stand-alone device, which may be used alone or in combination with an implement.
Figure 13:
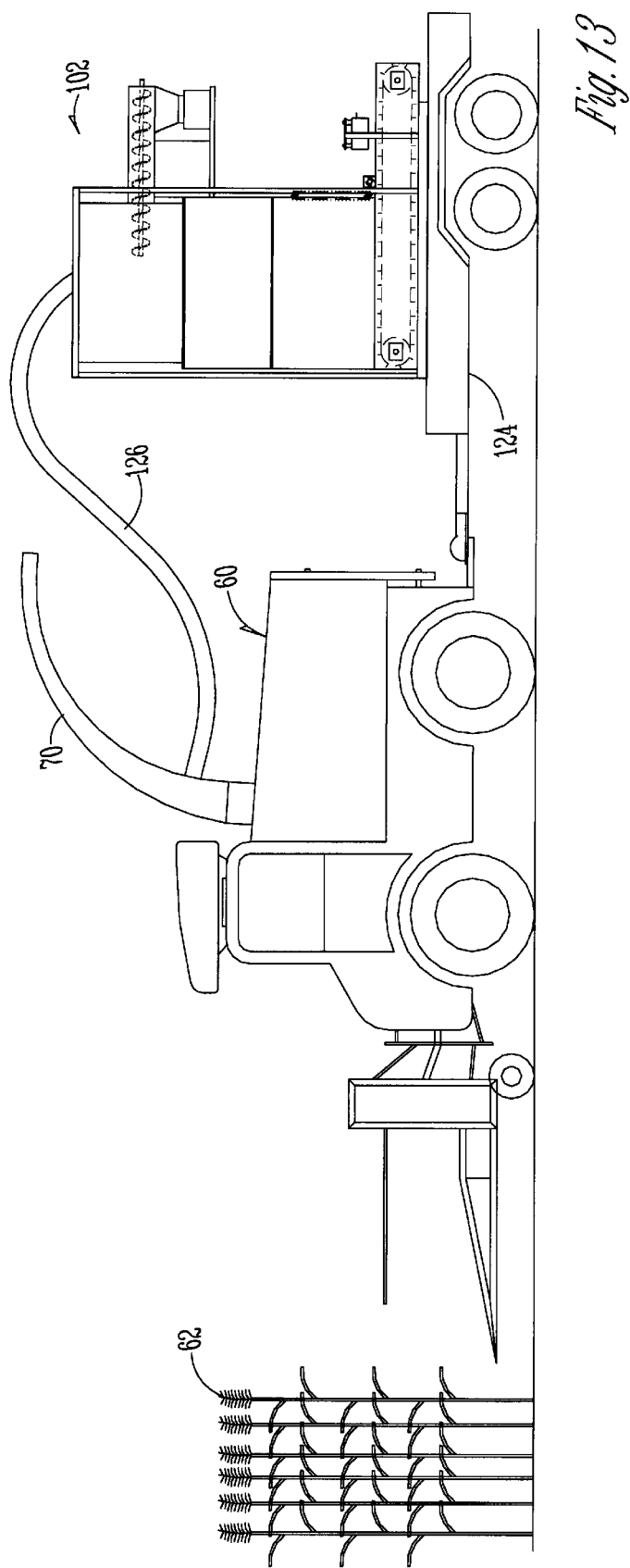

FIGS. 6–13 show alternate embodiments of the present invention. FIGS. 6–11 show the present invention used with a chopper, which is used to cut and chop forage. FIGS. 12–13 show a stand alone sampling unit (takes sub-samples, weighs the plot and records NIR spectra) that must be used in combination with an implement such as a chopper.

As opposed to grain, measuring constituents in forage is more difficult. Grain is more homogeneous than forage. Corn forage is comprised of a mixture of kernels, leaves, stalks, cobs, etc. of quite different particle sizes. This makes all of the parameters difficult to read. With forage, there are the additional required steps of grinding (to approximately 1 mm pieces) and drying the samples before sending the samples to a lab. These steps are not necessary with the present invention.

Figure 6:
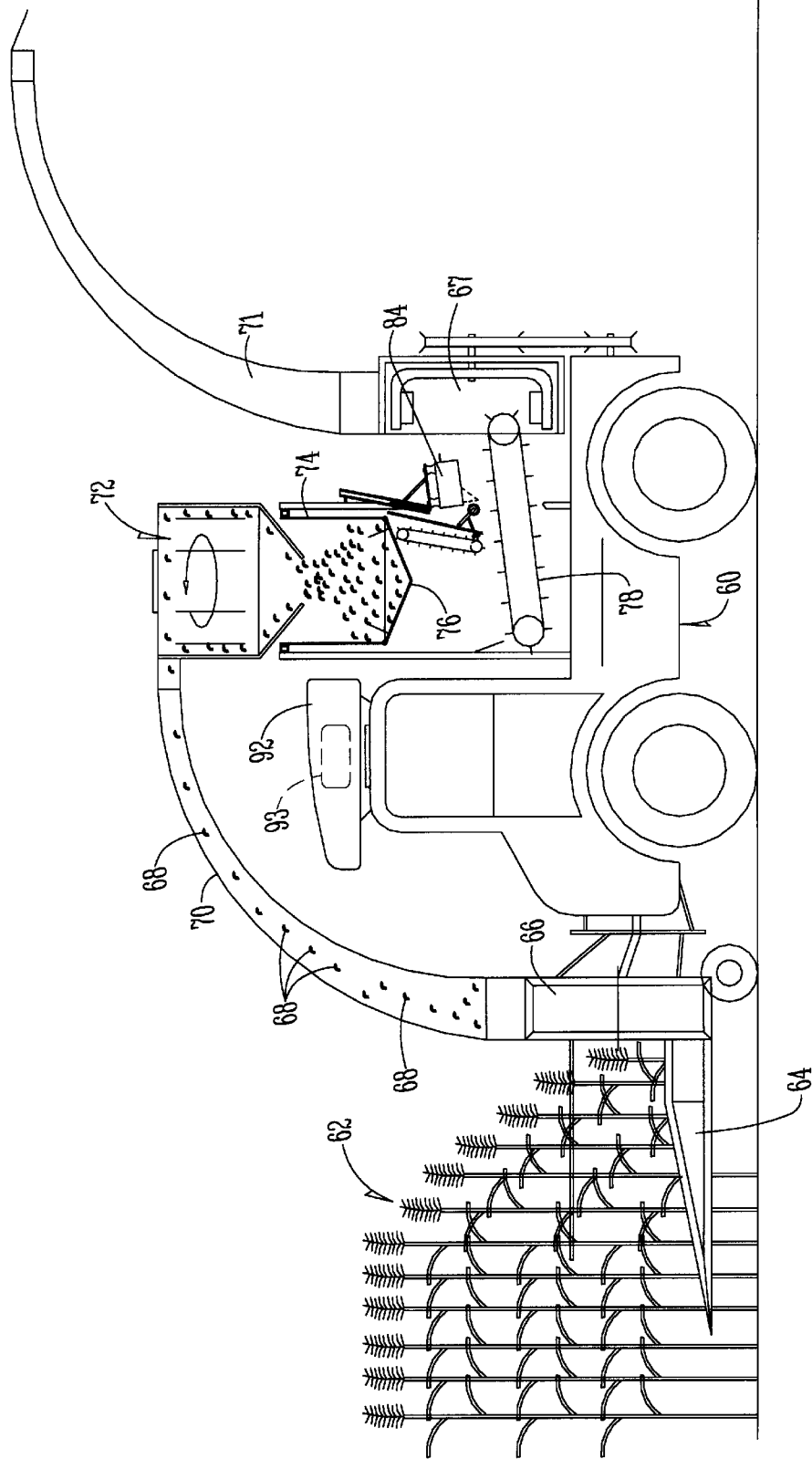
FIGS. 6–8 are side views of a research chopper utilizing the present invention.

FIG. 6 shows a chopper 60 being used to cut and chop forage 62. The chopper 60 is a Unimog model 1300 equipped with a forage cutting device. The chopper 60 includes a cutter 64 coupled to the front of the chopper 60. After the cutter 64 cuts the forage 62, a blower 66 blows the cut forage 68 through a pipe 70 and into a cyclone 72. The combination of the cutter 64 and cyclone 72 cuts the forage 68 into small pieces (approximately 5–10 mm). As the cut forage 68 falls through the cyclone 72, it is collected in a weigh box 74 having a pair of doors 76 disposed on the lower portion of the weigh box 74. FIG. 6 shows the doors 76 closed.

Figure 7:
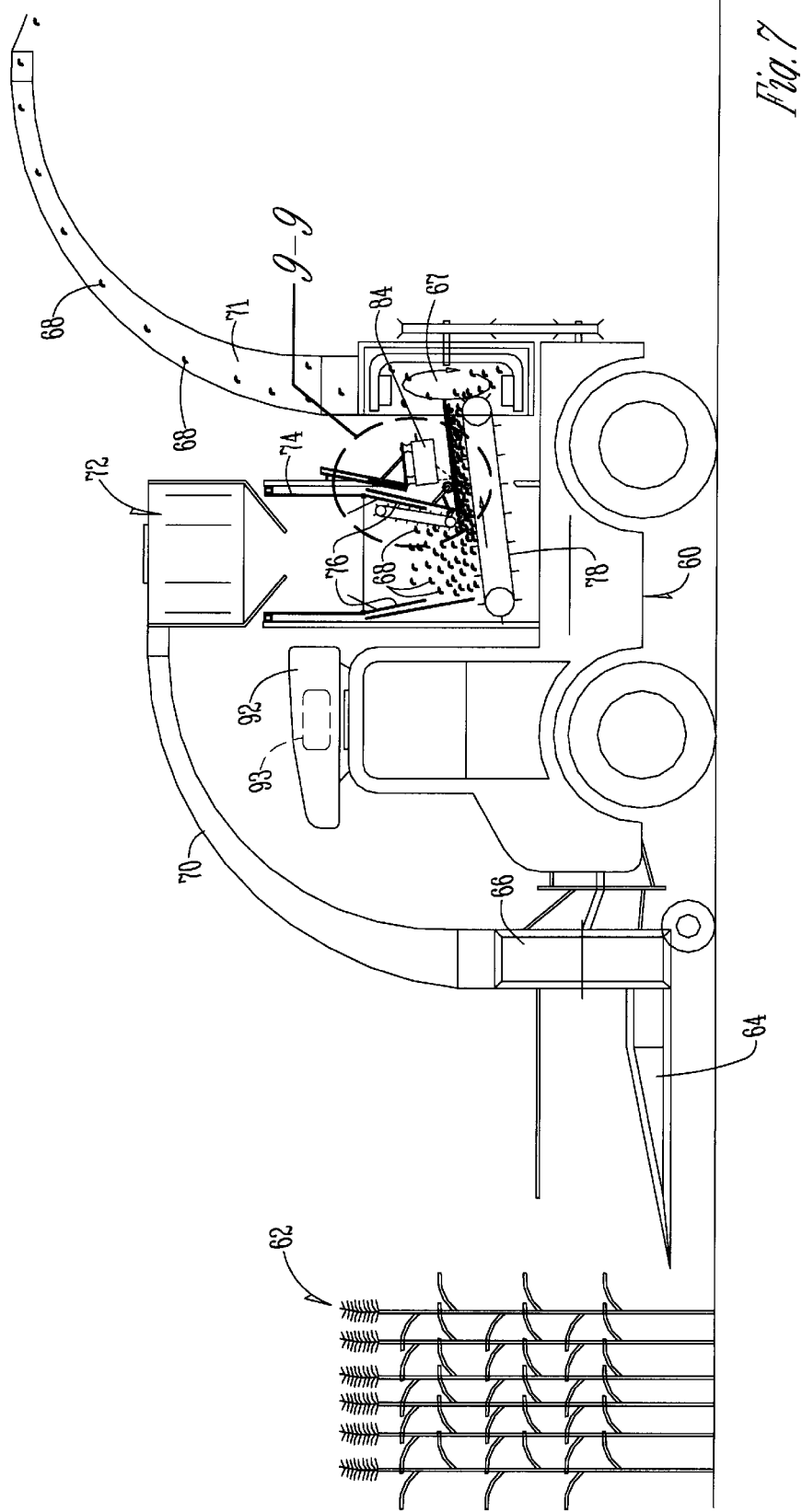
Figure 8:
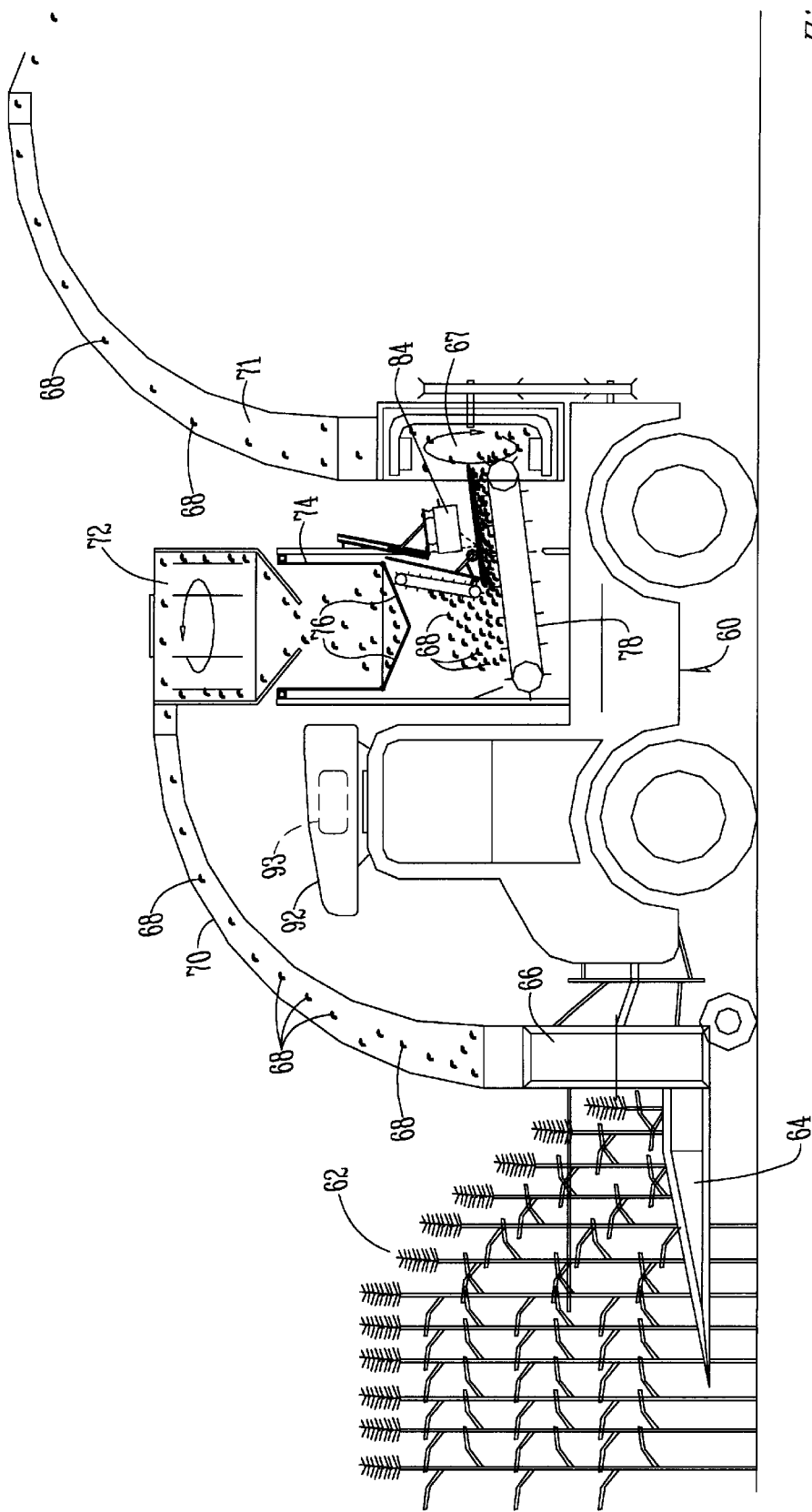
Figure 9:
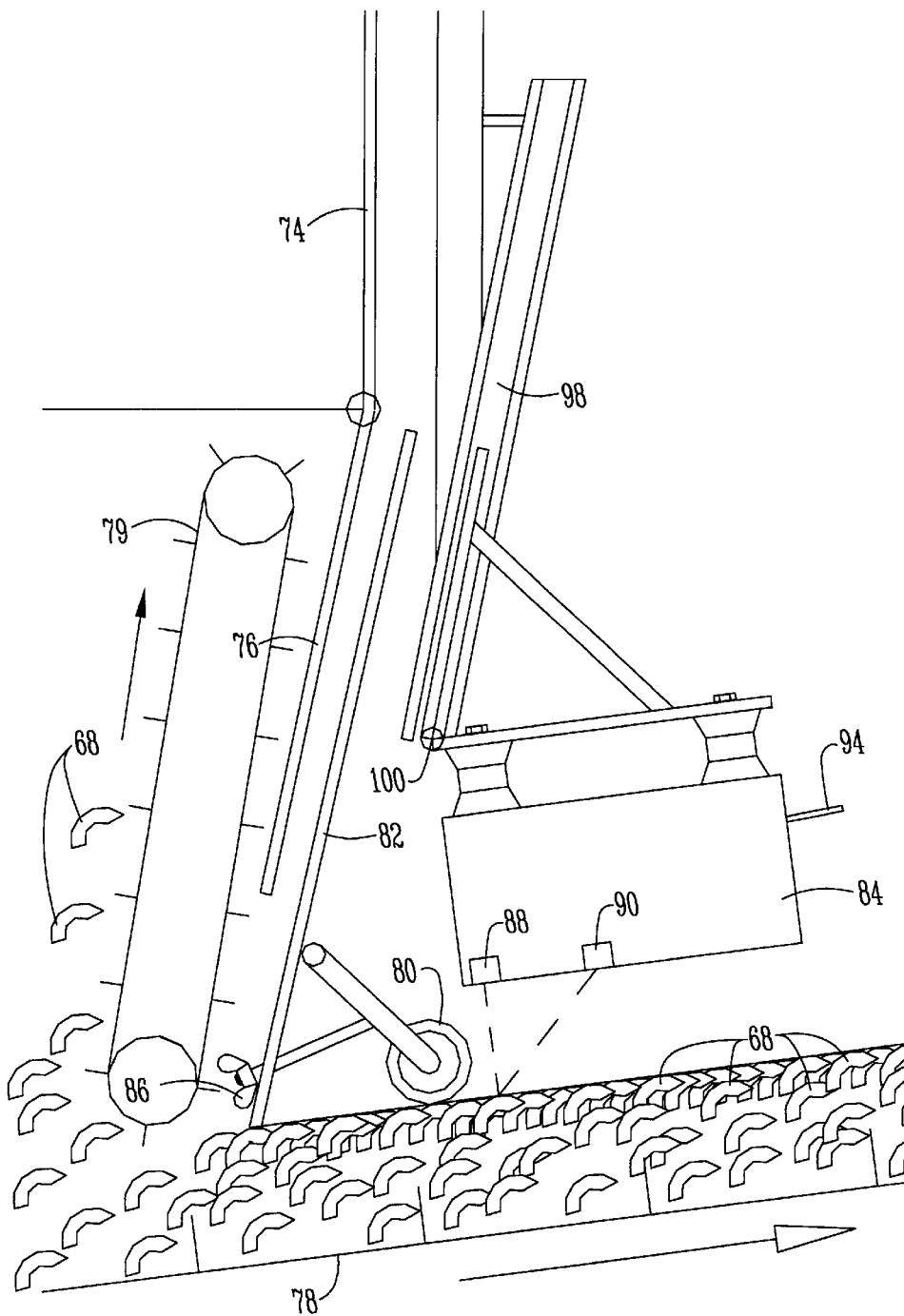
FIG. 9 is an enlarged view taken from lines 9—9 in FIG. 7.

After the cut forage 68 has been weighed in the weigh box 74, the doors 76 are opened and the cut forage 68 is dropped onto a conveyor belt 78 (FIG. 7). From the conveyor belt 78, the forage 68 is eventually blown through the pipe 71 by the blower 67. The forage 68 is then collected in a wagon (not shown). The chopper 60 has the capability of harvesting a subsequent test plot of forage 62 while measuring and testing the cut forage 68 from the previous plot (FIG. 8). FIG. 9 shows a close up of the conveyor belt 78 after the doors 76 have been opened. As shown, the cut forage 68 falls onto the conveyor belt 78. The conveyor belt moves to the right as illustrated by the arrow.

A wheel 80 along with a wall 82 and a substantially vertical conveyor 79 controls the level of the cut forage 68 as it passes underneath a monochromater 84. The wheel 80 and conveyor 79 insures a uniform distance between the cut forage 68 and the monochromater 84. In the preferred embodiment, this distance is set at 12 cm. As the cut forage 68 moves to the left on conveyor 78, the vertical conveyor 79 continuously scrapes off the upper layer of cut forage 68 to help ensure a uniform thickness of forage on the horizontal conveyor 78.

The monochromater 84 is analogous to the monochromater 32 described above. One suitable monochromater is the model DA7000 manufactured by Perten Instruments. Like the monochromater 32, the monochromater 84 includes a light source 88 and a light sensor 90. As light is transmitted by the light source 88, it reflects off the cut forage 68 and is detected by the light sensor 90. The reflected light can then be analyzed in a manner such as that described above. Major constituents that can be detected in the forage 68 include, but are not limited to, dry matter, starch content, NDF (natural detergent fiber) content, NDF digestibility, total plant digestibility, soluble sugars, crude protein, in addition to the ones mentioned above. In one embodiment, the monochromater 84 is connected to a computer 92 via a cable 94. The computer 92 may be mounted to a cooled box 93 as shown in FIGS. 6–8, within the cab of the chopper 60, or any other suitable location.

The monochromater 84 shown in FIG. 9 can be calibrated by using a white ceramic reference tile 96 similar to the tile 58 described above. FIGS. 10 and 11 show two alternate ways of calibrating the monochromater 84. In the embodiment shown in FIG. 10, the monochromater 84 is slid upward along a carriage sled 98. The white ceramic reference tile 96 is then placed in the position shown in FIG. 10 so that the monochromater 84 can be calibrated. As shown in FIG. 11, the monochromater 84 is also slid upward along the carriage sled 98, but then is also rotated counter clockwise about to the pivot point 100. The reference tile 96 is then placed in the orientation shown in FIG. 11 and the monochromater 84 is calibrated. After calibration, the monochromater 84 is moved back to the position shown in FIG. 9.

Like the embodiment shown in FIGS. 1–5, the embodiment shown in FIGS. 6–11 improves on accuracy and speed over the prior art. To help improve the accuracy of the system the forage sample presentation is made constant and repeatable. With the present invention, a much larger surface can be analyzed compared to the prior art. This is very important for heterogeneous materials such as corn forage. As a result of the consistency and repeatability, consistent results are obtained. The samples are sensed in the same way and in the same location for each successive sample. This is accomplished by constantly moving the cut forage samples 68 across the monochromater 84 as well as precisely controlling the distance between the monochromater 84 and the forage samples 68 via the vertical conveyor 79, the wheel 80, and wall 82. A consistent result is obtained by automating the analysis process. In addition, as described above, sensing the samples as the forage is moving improves the accuracy and reliability sensing. An "average" sample is taken, rather than looking at still samples, which may vary from one sample to the other. Since the samples can be analyzed at a high rate of speed, the processor can average a number of readings to obtain a consistent result for each sample. FIGS. 12 and 13 show a stand alone forage analysis device 102 being able to make following operations: weighs a test plot, takes sub-samples and records NIR spectra from a plot. The device 102 is similar in function to the device shown in FIGS. 6–11. The device is supported by a framework 104 which is rectangular shaped. Supported at the top of the framework 104 is a sampling device 106. During use, forage is loaded into the sampling device 106. A sampling auger 108 extends into the sampling device 106 and periodically is activated to draw sub-samples in to a sample storage container 110. Sub-samples are taken for each test plot in order to determine (at a later time) the relationship between light intensities and constituents in the samples.

Disposed below the sampling device 106 is weigh box 112, which is similar to the weigh box 74, described above. Disposed below the weigh box 112 is a storage bin 114, which stores the forage after being dumped from the weigh box 112. Doors (not shown) located at the bottom of the storage bin 114 periodically open to allow the forage to fall onto the conveyor 116. The conveyor 116 is similar to the conveyor 78 described above. As the conveyor 116 moves the forage, the vertical conveyor 118 and rolling mills 120 control the level of the forage as it passes underneath a monochromater 122. Like the wheel 80 and conveyor 79, the wheel mills 120 and conveyor 118 insure a uniform distance between the cut forage and the monochromater 122.

The stand alone forage analysis device 102 has to be used in combination with a chopper. The device 102 may be integrated with a chopper (i.e. placed on a chopper) similar to that shown in FIGS. 6–11 or the device 102 could also be pulled behind a chopper 60 on a trailer 124 (FIG. 13). As shown in FIG. 13, the device 102 is mounted on the trailer 124 and pulled behind the chopper 60. For the purposes of this description, the trailer 124 is considered to be part of the implement, which, in this example, is the chopper 60. Rather than blowing the cut forage through the pipe 70 (FIGS. 7–8), the cut forage is blown through a tube 126 and into the sampling device 106. The forage is then sampled and analyzed as described above.

As an alternative to using reflectance to measure constituents of product samples, light could be irradiated through the product samples and sensed after being transmitted through the samples. Also, various geometries of lamps and sensors could be used. The lamps and sensors could also be separated into two or more components rather than being contained in a single component such as the sensor heads 36 shown in the Figures. The number of fiber optic strands in each embodiment could also vary greatly. Other types of radiation could be used with the present invention other than NIR. For example Fourier Transform IR (FTIR) could be used. Also, the diffraction grating 38 could be replaced with other elements for spreading the light in the monochromator. The monochromator could also be replaced by various other types of sensors.

The foregoing examples illustrate the benefits of having real time measurement of constituents of substances in non-laboratory settings. The above applications can experience vibrations, some severe, and foreign material such as dust, dirt, and debris. This type of environment would make conventional NIR analysis susceptible of gross inaccuracies because of the need to have precise, controlled environmental conditions. In fact, measurements in environments such as crop fields, loading docks, on-board moving vehicles, or during product handling or transport can experience substantial physical forces which could knock conventional NIR equipment, with sensitive moving optical or other components, hopelessly out of calibration or even damage or make the equipment inoperative. Even if the measurement apparatus were stationary but the substance to be measured moved past the apparatus, forces can be created that would render the apparatus inaccurate.

Notwithstanding the above, environmental conditions in crop fields, loading docks, motor vehicles, pipelines, conveyors, and the like normally include air borne particles and dust, and vibrations or forces that make conventional laboratory NIR equipment unsuitable.

Therefore, while the prior description mentioned measurement on-board implements such as combines and choppers, or a stand-alone unit relative to agricultural products such as grain, similar benefits can be seen for other applications. For example, such non-destructive, real time measurements have been discussed as beneficial relative to hybrid development. Data can be taken and stored from test plots and analyzed. Similarly, it could be used for plant breeding programs and for precision farming. Constituents information in real time can be merged with field location information (e.g. using GPS) to track performance of certain varieties, track performance of certain fertilizer applications, and the like.

Furthermore, such non-destructive real time measurements in non-laboratory settings such as transport, storage, or other post-harvest times can provide important information. For example, measurement of constituents after a period of storage of an agricultural product can be used to improve storage methods. Potential buyers of an agricultural product could receive real time information about the constituents of the product they are buying. Moving the measurement apparatus or method by the product, or moving the product past or relative to the measurement apparatus or method, or both is possible.

Figure 14:
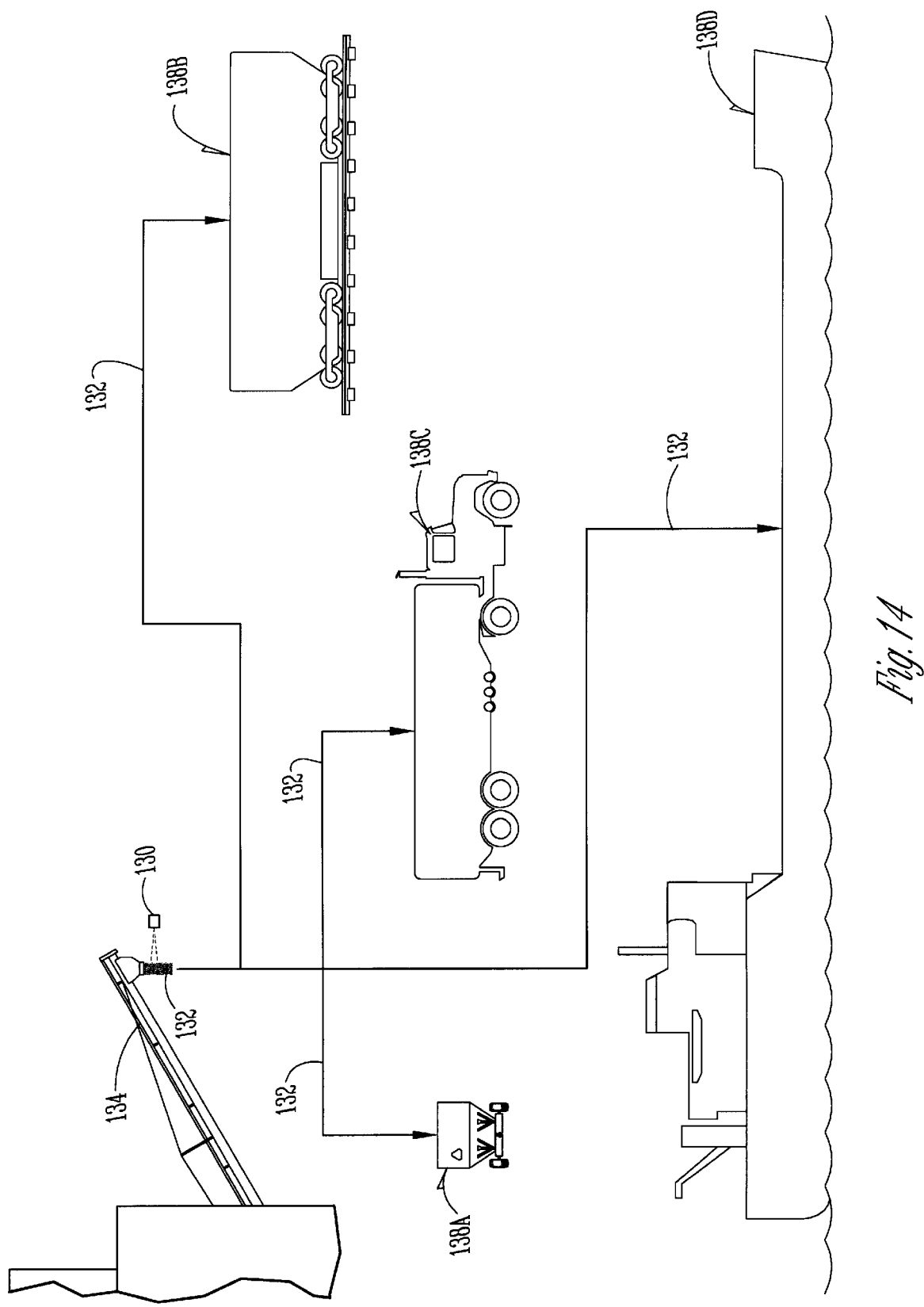
FIG. 14 is a diagrammatic view illustrating utilization of the invention relative to a substance moving to one of several exemplary transport vehicles.

For example, FIG. 14 diagrammatically illustrates a stationary measurement apparatus 130 according to the present invention placed near a stream of substance 132 that is flowing out of discharge member 134 (such as from an agricultural implement, from a storage bin, from a grain elevator, or at grain handling points). Constituent measurements could be taken as previously described, non-destructively and in real time as the substance 132 is directed to a transport vehicle 138. FIG. 14 shows but a few examples of transport vehicles, namely trailer 138A, rail car 138B, truck 138C, and barge 138D. Many others are possible.

Figure 15:
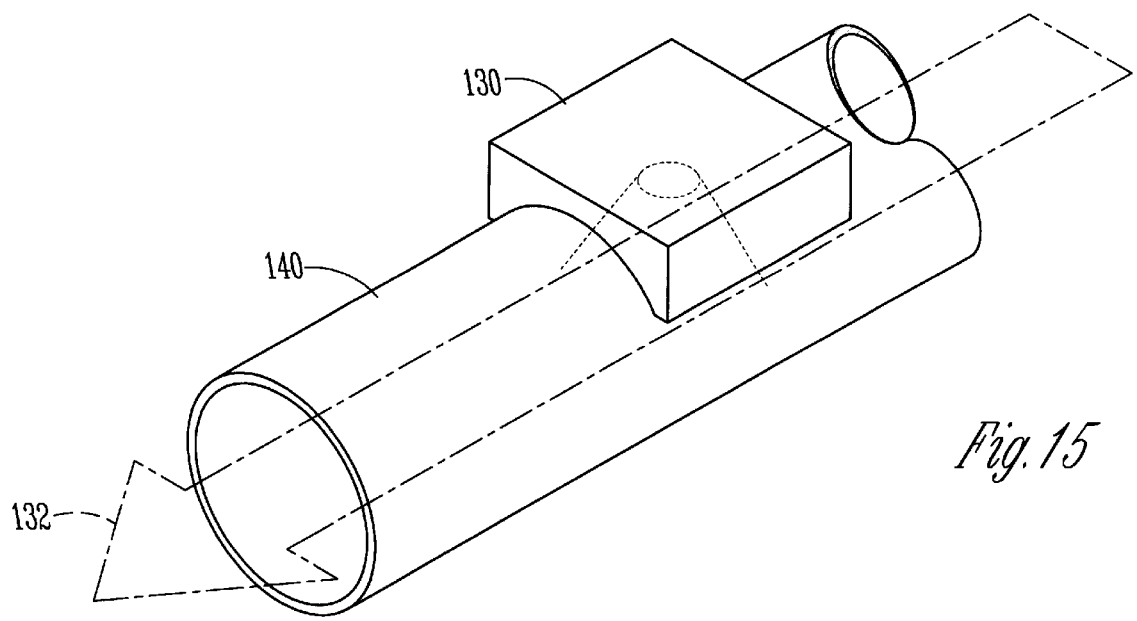
FIG. 15 is a diagrammatic view illustrating utilization of the invention relative to a substance moving in a transport vessel such as a pipeline.
Figure 16:
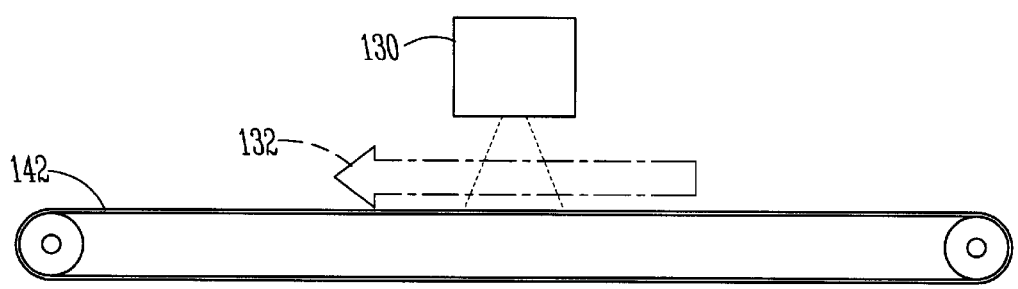
FIG. 16 is a diagrammatic view illustrating utilization of the invention relative to a substance moving on a transport vessel such as a conveyor.

FIG. 15 diagrammatically illustrates a stationary measurement apparatus 130 placed on or near what will be called a transport vessel for a substance 132. In this example, the transport vessel is a pipeline 140 where substance 132 flows or moves through pipeline 140. Again, despite the movement of substance 132, the real time, non-destructive constituent measurements can be taken. FIG. 16 illustrates another transport vessel for a substance 132, namely a conveyor 142.

Figure 17:
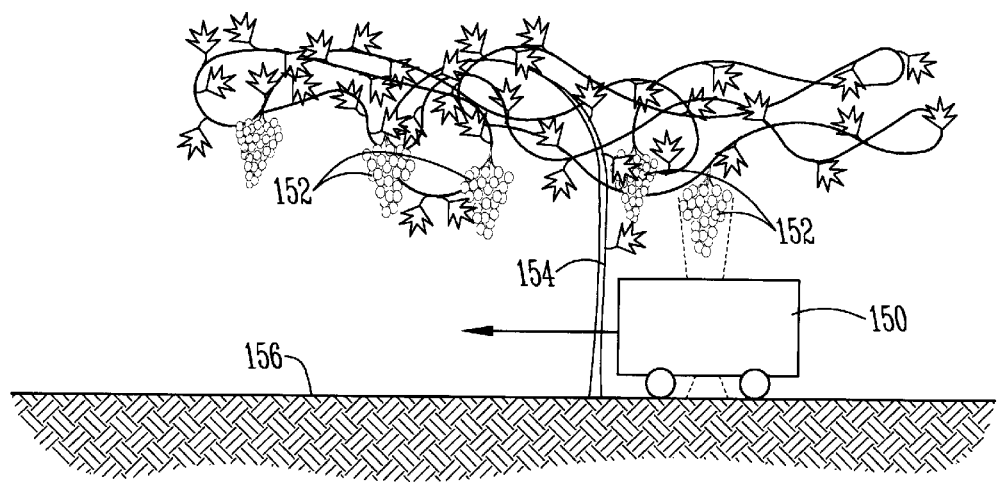
FIG. 17 is a diagrammatic view illustrating utilization of the invention moving relative to one of several exemplary substances or products.

Likewise, pre-harvest, non-destructive measurements in the agricultural product's own environment is possible. Sugar content of grapes on the vine can be measured before they are picked. FIG. 17 diagrammatically illustrates a moveable measurement apparatus 150 (for example on a trailer or a motor vehicle) that can be moved past fruit (such as grapes 152 on vines 154), irradiate fruit 152, receive the reflection of the NIR radiation, and process it as previously described. The fruit is not disturbed or touched, and the measurements are in real time. Another example is as follows. Levels of pharmaceutically active components induced to develop in plants (nutraceuticals) can be measured as the plants develop and before the pharmaceutically active components are harvested. These are but a few examples.

Another use would be to measure constituents of soil. This could replace the expenditure of resources of time and labor physically remove soil samples from the ground, transport them to a laboratory, and then evaluate them. Instead, the measurement apparatus 150 (see FIG. 17) could be moved across the soil 156 and the measurements taken non-destructively and in real-time, even though subject to vibration and dirt and other environmental conditions.

Figure 18:
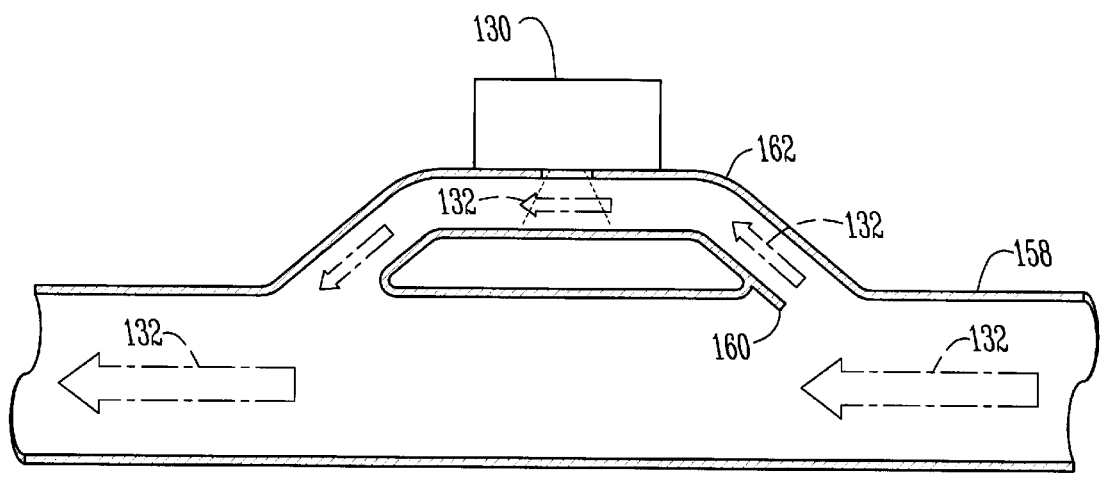
FIG. 18 is a diagrammatic view illustrating utilization of the invention relative to a diverted pathway from a main product pathway.

FIG. 18 illustrates another aspect of how the invention could be utilized. There are instances where a substance 132 is moved in a main path, such as in a main pipe 158. It would be possible to use a diverter 160 and divert a portion of the main flow of substance 132 into a secondary path, here pipe 162. A measurement apparatus 130 could be placed at or near pipe 162, measure constituents of substance 132 flowing in that secondary, diverted path in real time and non-destructively, and then allow the measured substance 132 to return to the main flow in pipe 162.

The preferred embodiment of the present invention has been set forth in the drawings and specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

For example, the spectral separator or monochromator discussed previously can be a diffraction grating without components or functions that are sensitive to vibration or other non-laboratory environment disturbances or forces that could make laboratory-type spectral separation equipment inaccurate or go out of calibration. It is particularly important that there be no optically sensitive moving components. The devices must be robust, stationary, solid state types of devices. Examples of apparatus that meet this criteria exist in the following classes of spectral separation methods—stationary interferometry, stationary Hadamard mask processes, acoustic-optic tunable filters (AOTF), and electro-optic modulation.

The preferred embodiment would have a robust, resistant-to-vibration, way to take the NIR energy reflected or passed through the substance being measured, splitting or separating that energy into discrete wavelengths or narrowly isolated portion or bands, and measuring characteristics of each isolated portion (e.g. intensity). This instrument especially must not be susceptible to vibration. Thus, it is preferred that the instrument have no moving optical parts. The methods mentioned above can be practiced according to the invention with no moving optical parts. A stationary grating and a detector with photodiode array are but one example of such an instrument.

As used herein, the term monochromator can refer to both isolating the portion of the NIR energy and detecting or measuring characteristics of the isolated portions. It sometimes is used when discussing just the isolating of the portions of the NIR energy.

What is claimed is:

1. An apparatus for measuring the constituents of a substance, said apparatus comprising:
    a light source capable of producing near infrared radiation in a controllable direction to a substance location;
    a sensor oriented towards the substance location, said sensor being capable of sensing near infrared radiation reflected from or passing through the substance location;
    a housing including a monochromator having no moving optical components, said monochromator being capable of isolating narrow portions of the near infrared spectrum, said monochromator being selected from the group consisting of a stationary interferometer, a stationary Hadamard mask, an acoustic-optic tunable filter (AOTF), and an electro-optic modulator, said housing further including a detector positioned to quantify and simultaneously detect one or more narrow portions of the near infrared spectrum created by the monochromator;

a communication member between the sensor and monochromator to transfer the sensed near infrared radiation to the monochromator; and a processor operatively connected to the monochromator, said processor being capable of identifying and determining the amount of constituents in the substance based on the quantified and simultaneously detected one or more isolated narrow portions of the near infrared spectrum;

wherein said housing is movable relative to the substance.

2. The apparatus of claim 1 wherein said monochromator is a stationary interferometer.

3. The apparatus of claim 1 wherein said monochromator is a stationary Hadamard mask.

4. The apparatus of claim 1 wherein said monochromator is an acoustic-optic tunable filter (AOTF).

5. The apparatus of claim 1 wherein said monochromator is an electro-optic modulator.

6. A method of analyzing a substance, said method comprising the steps of:

irradiating the substance with near infrared light;

with a sensor, sensing near infrared light, which reflects off or passes through the substance;

isolating simultaneously the sensed radiation into one or more narrow portions of the spectrum, said step of isolating being selected from the group consisting of using a stationary interferometer, using a stationary Hadamard mask, using an acoustic-optic tunable filter (AOTF), and using an electro-optic modulator;

analyzing one or more of the isolated narrow portions; and determining the identity and amount of constituents in the substance;

wherein the sensor is moved relative to the substance.

7. The method of claim 6 further comprising utilizing the constituents for agricultural product hybrid development.

8. The method of claim 6 further comprising utilizing the constituents for agricultural breeding programs.

9. The method of claim 6 further comprising utilizing the constituents for soil analysis.

10. The method of claim 6 further comprising utilizing the constituents for non-destructive analysis of nutraceuticals.

11. The method of claim 6 wherein the near infrared light is in the approximate range of 400 to 1700 nm in wavelength.

12. The method of claim 6 wherein said step of isolating is using a stationary interferometer.

13. The method of claim 6 wherein said step of isolating is using a stationary Hadamard mask.

14. The method of claim 6 wherein said step of isolating is using an acoustic-optic tunable filter (AOTF).

15. The method of claim 6 wherein said step of isolating is using an electro-optic modulator.

16. A method of analyzing constituents of a substance in real time in a non laboratory setting subject to diverse and changing environmental conditions, said method comprising the steps of:

irradiating the substance with near infrared light;

with a sensor, sensing near infrared light that reflects off or passes through the substance while moving the sensor relative to the substance;

isolating simultaneously the sensed radiation into one or more narrow portions of the spectrum, said step of isolating being selected from the group consisting of using a stationary interferometer, using a stationary Hadamard mask, using an acoustic-optic tunable filter (AOTF), and using an electro-optic modulator;

in real time, analyzing one ore more narrow portions of the spectrum; and determining the identity and amount of one or more constituents in the substance.

17. The method of claim 16 further comprising carrying a source for said near infrared light, the sensor and devises to isolate and analyze the sensed radiation on a mobile carrier,which can be moved past the substance.

18. The method of claim 16 wherein said step of isolating is using a stationary interferometer.

19. The method of claim 16 wherein said step of isolating is using a stationary Hadamard mask.

20. The method of claim 16 wherein said step of isolating is using an acoustic-optic tunable filter (AOTF).

21. The method of claim 16 wherein said step of isolating is using an electro-optic modulator.

22. A system for measuring constituents of substances in real time in a non-laboratory setting subject to diverse and changing environmental conditions, said system comprising;

a light source capable of producing near infrared radiation in a controllable direction to a substance location;

a sensor oriented towards the substance location and capable of sensing near infrared radiation reflected from or passing through a substance at a substance location;

a monochromator having no moving optical components, said monochromator being selected from the group consisting of a stationary interferometer, a stationary Hadamard mask, an acoustic-optic tunable filter (AOTF), and an electro-optic modulator, said monochromator being capable of isolating narrow portions of the near infrared spectrum and having a detector positioned to quantify and simultaneously detect one or more isolated narrow portions of the near infrared spectrum created by the monochromator;

a communication member between the sensor and the monochromator to transfer the sensed near infrared radiation to the monochromator; and a processor operatively connected to the monochromator, said processor being capable of identifying and determining the amount of the constituents in the product based on the quantified and simultaneously detected one or more isolated narrow portions of the infrared spectrum.

23. The system of claim 22 wherein said monochromator is a stationary interferometer.

24. The system of claim 22 wherein said monochromator is a stationary Hadamard mask.

25. The system of claim 22 wherein said monochromator is an acoustic-optic tunable filter (AOTF).

26. The system of claim 22 wherein said monochromator is an electro-optic modulator.

* * * * *

(12) EX PARTE REEXAMINATION CERTIFICATE (9909th)
United States Patent
Wright et al.

(10) Number: US 6,483,583 C1
(45) Certificate Issued: Oct. 25, 2013

(54) NEAR INFRARED SPECTROMETRY FOR REAL TIME ANALYSIS OF SUBSTANCES

(75) Inventors: Steven L. Wright, West Des Moines, IA (US); Thomas B. Brumback, Jr., Alleman, IA (US); William S. Niebur, Des Moines, IA (US); Roland Welle, Buxtehude (DE)

(73) Assignee: Textron Systems Corporation, Wilmington, MA (US)

Reexamination Request:
No. 90/020,023, Sep. 14, 2012

Reexamination Certificate for:
Patent No.: 6,483,583
Issued: Nov. 19, 2002
Appl. No.: 09/309,157
Filed: May 10, 1999

Related U.S. Application Data

(63) Continuation-in-part of application No. 09/075,614, filed on May 11, 1998, now Pat. No. 5,991,025, which is a continuation-in-part of application No. 08/807,661, filed on Feb. 27, 1997, now Pat. No. 5,751,421.

(51) Int. Cl.
*G01J 3/28* (2006.01)
*A01F 12/00* (2006.01)

(52) U.S. Cl.
USPC .............................. 356/326; 356/328; 460/7

(58) Field of Classification Search
None
See application file for complete search history.

(56) References Cited

To view the complete listing of prior art documents cited during the proceeding for Reexamination Control Number 90/020,023, please refer to the USPTO's public Patent Application Information Retrieval (PAIR) system under the Display References tab.

*Primary Examiner* — Angela M Lie

(57) ABSTRACT

An apparatus and method for utilizing NIR spectrography for measuring major constituents of substances in real time includes a monochromator or other sensor having no moving optical parts. At least one of the monochromator and the substance are moving relative to one another. An NIR radiation source irradiates a substance and the reflected or passed-through radiation is transmitted to the monochromator, which isolates and detects narrow portions of the received spectrum. By analyzing the intensities and wavelengths of the received radiation, the presence and amount of major constituents of the substance can be determined.

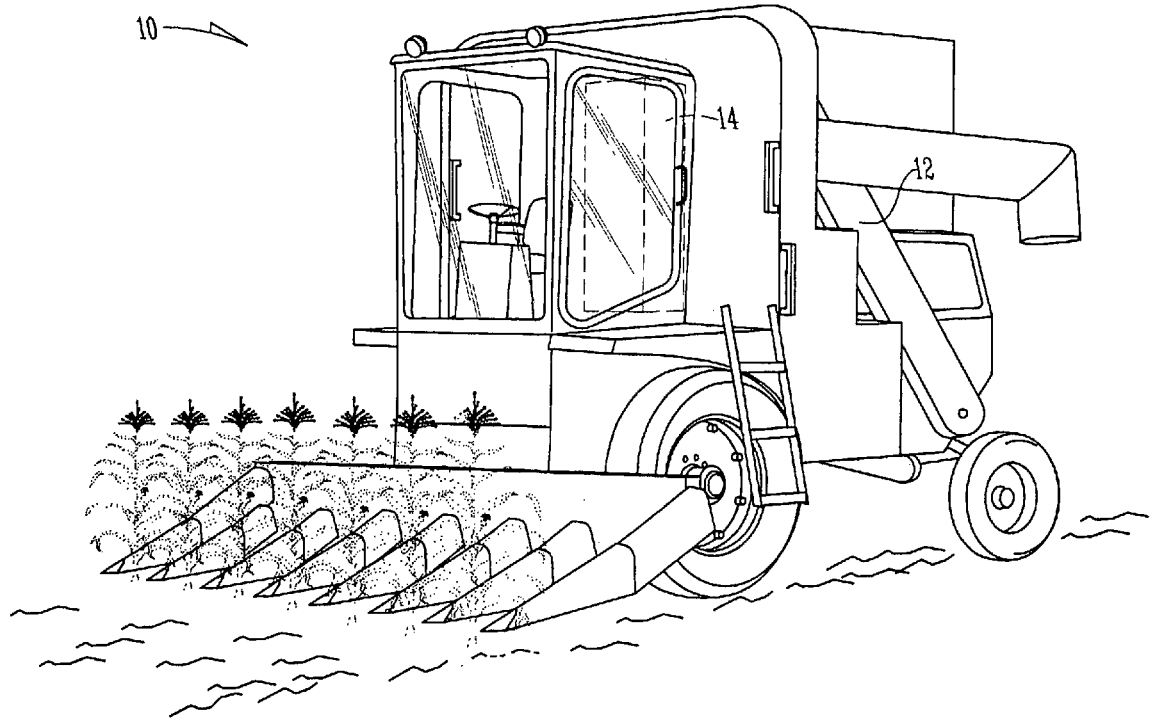

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1-15 and 17 is confirmed.

Claims 16 and 18-26 are cancelled.

* * * * *